(12) United States Patent     (10) Patent No.: US 12,638,407 B2

Watanabe et al.     (45) Date of Patent: May 26, 2026

(54) OIL CONDITION DETERMINATION SYSTEM AND OIL CONDITION DETERMINATION METHOD

(71) Applicant: NIPPON PILLAR PACKING CO., LTD, Osaka (JP)

(72) Inventors: Kentaro Watanabe, Osaka (JP); Akira Nakatsu, Osaka (JP); Yusuke Natsuhara, Osaka (JP); Yusuke Tokuda, Osaka (JP)

(73) Assignee: PILLAR Corporation, Osaka (JP)

( * ) Notice: Subject to any disclaimer, the term of this patent is extended or adjusted under 35 U.S.C. 154(b) by 283 days.

(21) Appl. No.: 18/635,250

(22) Filed: Apr. 15, 2024

(65) Prior Publication Data

US 2024/0361268 A1     Oct. 31, 2024

(30) Foreign Application Priority Data

Apr. 25, 2023     (JP) ................................. 2023071805

(51) Int. Cl.
    *G01N 27/06*       (2006.01)
    *G01N 27/04*       (2006.01)
    *G01N 33/28*       (2006.01)

(52) U.S. Cl.
    CPC ........... *G01N 27/06* (2013.01); *G01N 27/046* (2013.01); *G01N 33/2888* (2013.01)

(58) Field of Classification Search
    CPC ...... F16N 29/00; G01N 27/046; G01N 27/06; G01N 33/2888
    See application file for complete search history.

(56) References Cited

U.S. PATENT DOCUMENTS

| | | | |
|---|---|---|---|
| 11,802,863 B2 | 10/2023 | Sasaki et al. | |
| 2006/0232267 A1* | 10/2006 | Halalay | G01N 33/2888 |
| | | | 508/110 |
| 2020/0363390 A1* | 11/2020 | Sasaki | G01N 27/06 |

FOREIGN PATENT DOCUMENTS

| | | |
|---|---|---|
| JP | S6120848 A | 1/1986 |
| JP | H1078402 A | 3/1998 |
| JP | 6910037 B2 | 7/2021 |

* cited by examiner

*Primary Examiner* — Eman A Alkafawi
*Assistant Examiner* — Courtney G Mcdonnough
(74) *Attorney, Agent, or Firm* — NKL Law; Allen Xue

(57)       ABSTRACT

Provided are an oil condition determination system and an oil condition determination method that are capable of continuously determining the oil condition when oil is partially replaced or oil is added. An oil condition determination system includes a measurement unit and a determination unit. The measurement unit periodically measures a resistance value of oil. The determination unit periodically determines a condition of the oil based on the resistance value, stores a local maximum value of the resistance value, determines that the condition of the oil has changed when a difference between the local maximum value and the resistance value becomes greater than or equal to a first threshold value, and initializes the local maximum value and updates the first threshold value when the amount of change in the resistance value per unit time becomes greater than or equal to a second threshold value.

9 Claims, 8 Drawing Sheets

OIL CONDITION DETERMINATION SYSTEM AND OIL CONDITION DETERMINATION METHOD

TECHNICAL FIELD

The present invention relates to an oil condition determination system and an oil condition determination method.

BACKGROUND ART

JP S61-20848A discloses an apparatus for determining the degree of deterioration of lubricating oil. This apparatus for determining the degree of deterioration applies an alternating-current voltage to a pair of electrodes in contact with lubricating oil and determines the degree of deterioration of the lubricating oil based on a current generated in the electrodes.

JP S61-20848A is an example of related art.

SUMMARY OF THE INVENTION

A method to determine the condition of oil based on the resistance value of the oil is conceivable. However, when oil is partially replaced or oil is added, the transition of the resistance value of the oil changes. If the transition of the resistance value changes, it may not be possible to properly determine the oil condition based on the same criterion as that before oil is partially replaced or oil is added. JP S61-20848A above does not disclose any means for solving such an issue.

The present invention was made in order to solve the above-described problem, and it is an object thereof to provide an oil condition determination system and an oil condition determination method that are capable of continuously determining the oil condition even when oil is partially replaced or oil is added.

An oil condition determination system according to an aspect of the present invention includes a measurement unit and a determination unit. The measurement unit periodically measures a resistance value of oil. The determination unit periodically determines a condition of the oil based on the resistance value. The determination unit stores a local maximum value of the resistance value, determines that the condition of the oil has changed in a case in which a difference between the local maximum value and the resistance value becomes greater than or equal to a first threshold value, and initializes the local maximum value and updates the first threshold value in a case in which the amount of change in the resistance value per unit time becomes greater than or equal to a second threshold value.

When oil is partially replaced or oil is added, the resistance value of the oil may abruptly change. In this oil condition determination system, the local maximum value is initialized and the first threshold value is updated if the amount of change in the resistance value per unit time becomes greater than or equal to the second threshold value. That is to say, when the resistance value abruptly changes due to oil being partially replaced or oil being added, the determination criterion for the oil condition is properly changed. Therefore, according to this oil condition determination system, the oil condition can be continuously and properly determined even when oil is partially replaced or oil is added.

In the oil condition determination system described above, it is also possible that the determination unit updates the first threshold value based on the amount of change in a case in which the amount of change becomes greater than or equal to the second threshold value.

When oil is partially replaced or oil is added, the transition of the resistance value of the oil changes in accordance with the amount of oil replaced or the amount of oil added. According to this oil condition determination system, the first threshold value is updated based on the amount of change correlated with the amount of oil replaced or the amount of oil added, and the determination criterion for the oil condition is more properly changed. Accordingly, the oil condition can be more properly determined.

It is also possible that the oil condition determination system described above further includes a notification unit configured to notify a user that the oil needs to be replaced in a case in which the determination unit determines that the condition of the oil has changed.

According to this oil condition determination system, the user is notified that the oil needs to be replaced in the case in which it is determined that the condition of the oil has changed, and thus the user can be prompted to replace oil at the time at which oil replacement becomes necessary.

In the oil condition determination system described above, it is also possible that, in a case in which a difference between the local maximum value and the resistance value becomes greater than or equal to the first threshold value, the determination unit determines that the condition of the oil has changed when a decrease in the resistance value has continued for a predetermined period of time, and does not determine that the condition of the oil has changed when a decrease in the resistance value has not continued for the predetermined period of time.

The resistance value of oil may temporarily decrease and then increase when oil is added. Even when a difference between the local maximum value and the resistance value becomes greater than or equal to the first threshold value due to the resistance value of the oil temporarily decreasing, it is not always appropriate to determine that the condition of the oil has changed if the resistance value increases thereafter. According to this oil condition determination system, even when a difference between the local maximum value and the resistance value becomes greater than or equal to the first threshold value, it is not determined that the condition of the oil has changed if a decrease in the resistance value has not continued for the predetermined period of time, and thus the occurrence of the above-mentioned inappropriate situation can be suppressed.

In the oil condition determination system described above, it is also possible that the determination unit determines that the condition of the oil has changed in a case in which a difference between the local maximum value and the resistance value becomes greater than or equal to the first threshold value and a trend of change in the resistance value reverses.

An oil condition determination method according to another aspect of the present invention includes a step of periodically measuring a resistance value of oil and a step of periodically determining a condition of the oil based on the resistance value. The step of periodically determining a condition of the oil includes a step of storing a local maximum value of the resistance value, a step of determining that the condition of the oil has changed in a case in which a difference between the local maximum value and the resistance value becomes greater than or equal to a first threshold value, and a step of initializing the local maximum value and updating the first threshold value in a case in which the amount of change in the resistance value per unit time becomes greater than or equal to a second threshold value.

In this oil condition determination method, the local maximum value is initialized and the first threshold value is updated if the amount of change in the resistance value per unit time becomes greater than or equal to the second threshold value. That is to say, when the resistance value abruptly changes due to oil being partially replaced or oil being added, the determination criterion for the oil condition is properly changed. Therefore, according to this oil condition determination method, the oil condition can be properly determined even when oil is partially replaced or oil is added.

According to the present invention, it is possible to provide an oil condition determination system and an oil condition determination method that are capable of continuously determining the oil condition even when oil is partially replaced or oil is added.

EMBODIMENTS OF THE INVENTION

Figure 1:
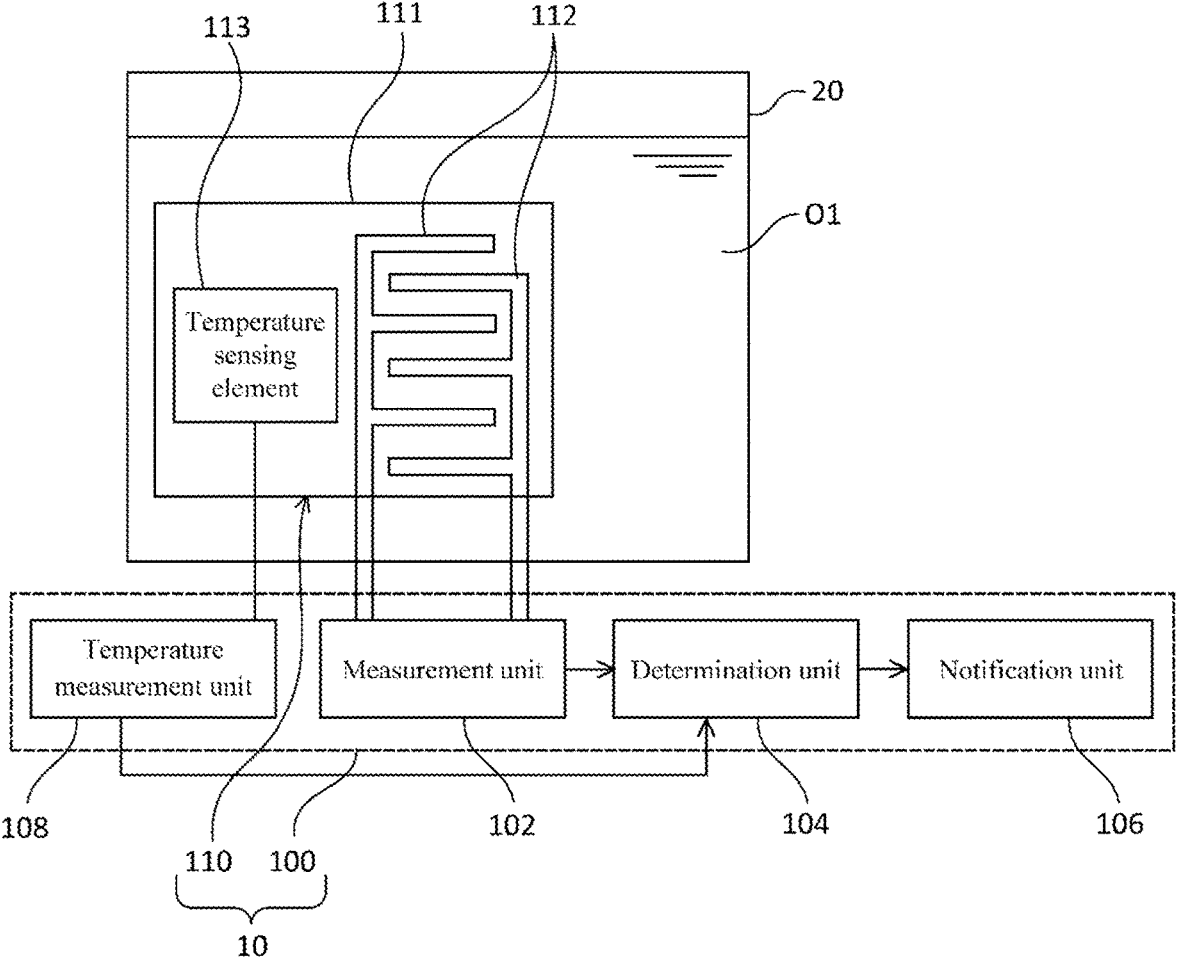
FIG. 1 is a diagram schematically showing the configuration of an oil sensor including an oil condition determination system.

An embodiment according to one aspect of the present invention (hereinafter also referred to as "the present embodiment") will be described in detail below with reference to the drawings. Note that the same or corresponding elements in the drawings are denoted by the same reference numerals, and descriptions will not be repeated for such elements. Also, the illustrations in the drawings are schematic illustrations with elements omitted or exaggerated as appropriate to facilitate understanding.

1. Configuration of Oil Condition Determination System

FIG. 1 is a diagram schematically showing the configuration of an oil sensor 10 including an oil condition determination system 100 according to the present embodiment. The oil sensor 10 is installed in an oil tank 20 of a vehicle or the like, for example, and is configured to detect the condition (the degree of deterioration) of oil O1. The oil sensor 10 detects the condition of the oil O1 in a state of being at least partially immersed in the oil O1.

As shown in FIG. 1, the oil sensor 10 includes the oil condition determination system 100 and a substrate 110. When the oil sensor 10 is in use, the substrate 110 is immersed in the oil O1. The substrate 110 is, for example, substantially rectangular in plan view. The substrate 110 includes a substrate body 111, a pair of electrodes 112, and a temperature sensing element 113. The substrate body 111 is a so-called fluoroplastic substrate. Since fluoroplastic substrates have excellent weather and chemical resistance, the substrate 110 including the substrate body 111 can withstand use in a harsh environment. The substrate body 111 does not necessarily have to be constituted by a fluoroplastic substrate, but is preferably constituted by a substrate with excellent chemical resistance, for example.

The pair of electrodes 112 are formed on the substrate body 111. The pair of electrodes 112 are used to measure the electrical resistance value (hereinafter also referred to simply as a "resistance value") of the oil O1. The electrodes 112 are comb-shaped. In the substrate 110, the pair of electrodes 112 are arranged such that the tooth portions of the electrodes 112 are positioned alternatingly. The pair of electrodes 112 are formed by patterning a conductive layer formed on one face of the substrate body 111, for example.

The temperature sensing element 113 is mounted on the substrate body 111. The temperature sensing element 113 is used to measure the temperature of the oil O1. The temperature sensing element 113 is constituted by an electrical temperature sensor such as a resistance temperature detector (RTD), a thermistor, or a thermocouple, for example.

The oil condition determination system 100 includes a measurement unit 102, a temperature measurement unit 108, a determination unit 104, and a notification unit 106. The measurement unit 102 includes a power source, an ammeter, and a calculation circuit, for example. The measurement unit 102 applies a measurement voltage between the pair of electrodes 112 and measures a current generated in a circuit including the pair of electrodes 112. The measurement unit 102 detects the resistance value (impedance) between the pair of electrodes 112 based on the voltage applied between the pair of electrodes 112 and the measured current. That is to say, the measurement unit 102 measures the resistance value between the pair of electrodes 112. When the pair of electrodes 112 are entirely immersed in the oil O1, the resistance value between the pair of electrodes 112 is considered to be the resistance value of the oil O1. In the present embodiment, the measurement voltage applied between the pair of electrodes 112 is an alternating-current voltage. Note that the measurement voltage does not necessarily have to be an alternating-current voltage, and may be a direct-current voltage.

The temperature measurement unit 108 applies a measurement voltage to the temperature sensing element 113 and measures a current generated in a circuit including the temperature sensing element 113, for example. The temperature measurement unit 108 detects the resistance value of the temperature sensing element 113, for example, based on the voltage applied to the temperature sensing element 113 and the measured current. That is to say, the temperature measurement unit 108 measures, for example, the resistance value of the temperature sensing element 113.

The determination unit 104 includes a CPU (Central Processing Unit), a RAM (Random Access Memory), and a ROM (Read Only Memory), for example. The determination unit 104 measures the temperature of the oil O1 based on the resistance value measured by the temperature measurement unit 108. For example, a relationship between the temperature and the resistance value is stored in advance in the determination unit 104. How information on the temperature of the oil O1 is used will be explained later. The determination unit 104 determines the condition of the oil O1 based on the resistance value measured by the measurement unit 102. The determination unit 104 determines whether or not the oil O1 contained in the oil tank 20 needs to be replaced, for example. The determination procedure by the determination unit 104 will be described later in detail.

The notification unit 106 includes a display, for example. The notification unit 106 notifies the user of a determination result by, for example, displaying an image showing the determination result produced by the determination unit 104. According to the oil condition determination system 100, for example, if it is determined that the oil O1 needs to be replaced, the user is notified to that effect, and thus the user can be prompted to replace oil at the time at which oil replacement becomes necessary.

2. Adjustment of Determination Criterion for Oil Condition

Figure 2:
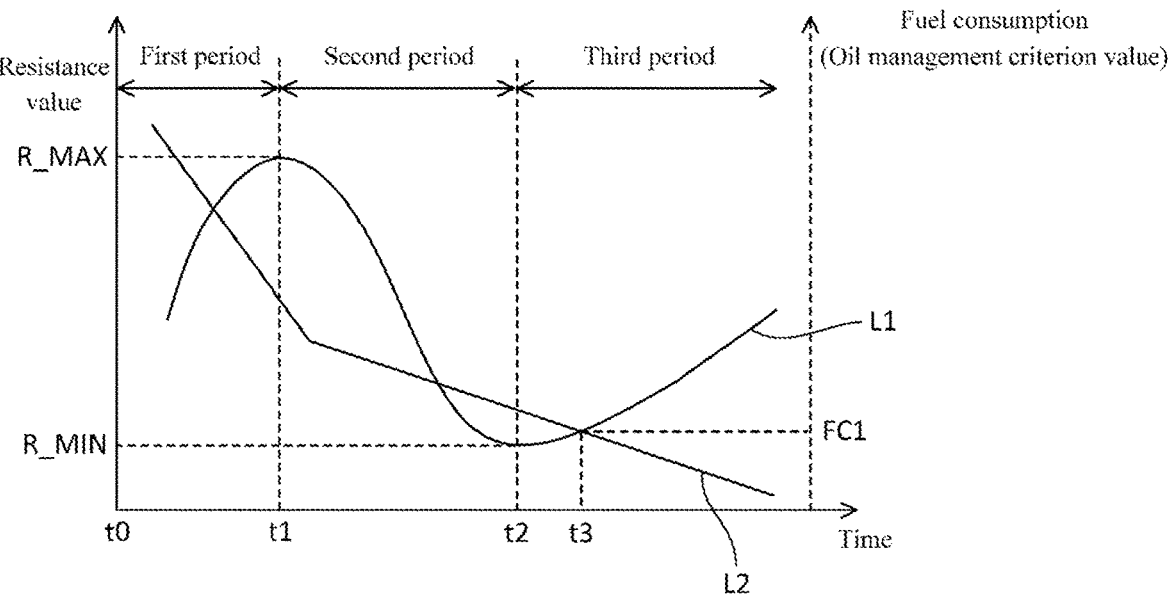
FIG. 2 is a diagram showing an example of a relationship between the change over time in a resistance value of oil and the change over time in fuel consumption.

FIG. 2 is a diagram showing an example of a relationship between the change over time in the resistance value of the oil O1 and the change over time in fuel consumption. Referring to FIG. 2, the horizontal axis indicates the time of use of the oil O1, one of the vertical axes indicates the resistance value of the oil O1, and the other vertical axis indicates the fuel consumption. A line L1 shows a relationship between the resistance value and the time of use of the oil O1, and a line L2 shows a relationship between the fuel consumption and the time of use. Note that the time of use of the oil O1 is the time during which the oil O1 is actually used. For example, if the oil O1 is engine oil, the time of use is the time during which a vehicle is being driven by the engine.

In a first period (time t0 to t1), the resistance value of the oil O1 increases. The increase in the resistance value in the first period is caused, for example, by the consumption (decrease) of additives contained in the oil O1.

In a second period (time t1 to t2), the trend of change in the resistance value reverses (turns from an increase to a decrease), and the resistance value decreases. The decrease in the resistance value in the second period is caused, for example, by oxidation (an increase in oxidation products) of the oil O1.

In a third period (time t2 and thereafter), the trend of change in the resistance value reverses again (turns from a decrease to an increase), the resistance value increases. The increase in the resistance value in the third period is caused, for example, by an increase in sludge in the oil O1.

Such a correlation exists between the resistance value and the time of use of the oil O1. That is to say, when the oil O1 is continuously used, the resistance value of the oil O1 temporarily increases, after which the resistance value turns from an increase to a decrease and turns again from a decrease to an increase, as the time of use elapses. For example, it is conceivable that the condition of the oil O1 is considered to have changed to a deteriorated condition at the time at which the resistance value turns from a decrease to an increase. That is to say, it is conceivable that the user is prompted to replace the oil O1 at the time at which the resistance value turns from a decrease to an increase.

In the example shown in FIG. 2, the fuel consumption is used as the oil management criterion value, and it is preferable that the oil is replaced, for example, before the fuel consumption reaches a value that is less than or equal to FC1. In this example, the fuel consumption reaches a value that is less than or equal to FC1 at time t3. On the other hand, the time at which the resistance value of the oil O1 turns from a decrease to an increase is time t2. Time t2 is earlier than time t3. In this case, there is no problem if the user is prompted to replace the oil O1 at the time (time t2) at which the resistance value of the oil O1 turns from a decrease to an increase.

Figure 3:
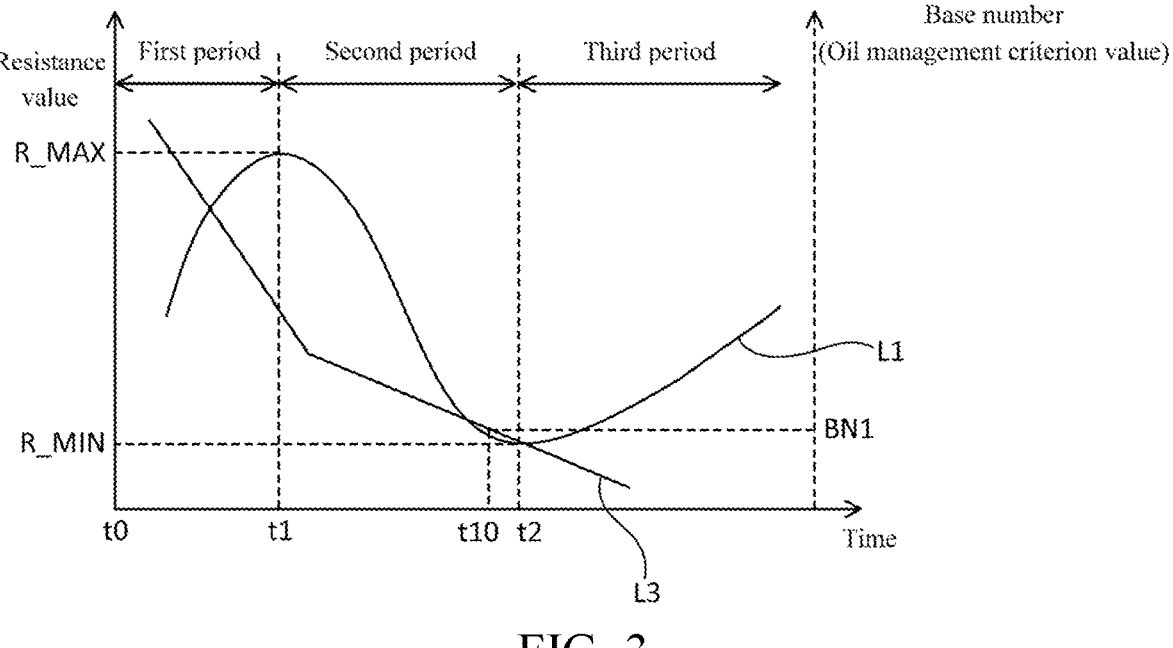
FIG. 3 is a diagram showing an example of a relationship between the change over time in a resistance value of oil and the change over time in the base number of the oil.

FIG. 3 is a diagram showing an example of a relationship between the change over time in the resistance value of the oil O1 and the change over time in the base number of the oil O1. Referring to FIG. 3, the horizontal axis indicates the time of use of the oil O1, one of the vertical axes indicates the resistance value of the oil O1, and the other vertical axis indicates the base number of the oil O1. Aline L3 shows a relationship between the base number and the time of use of the oil O1.

In the example shown in FIG. 3, the base number of the oil O1 is used as the oil management criterion value, and it is preferable that the oil is replaced, for example, before the base number reaches a value that is less than or equal to BN1. In this example, the base number reaches a value that is less than or equal to BN1 at time t10. On the other hand, the time at which the resistance value of the oil O1 turns from a decrease to an increase is time t2. Time t2 is later than time t10. In this case, even if the user is prompted to replace the oil O1 at the time (time t2) at which the resistance value turns from a decrease to an increase, the proper replacement timing (time t10) has already passed. As a result, for example, the deterioration of the equipment using the oil O1 is accelerated.

In the oil condition determination system 100 according to the present embodiment, a change in the condition of the oil O1 is not determined based on whether or not the resistance value of the oil O1 has turned from a decrease to an increase. In the oil condition determination system 100, the difference between the local maximum value of the resistance value and the resistance value is periodically detected, and if the difference between the local maximum value and the resistance value becomes greater than or equal to a first threshold value, it is determined that the condition of the oil O1 has changed (has deteriorated). The first threshold value can be said to be a threshold value for determining a change in the condition of the oil O1.

Figure 4:
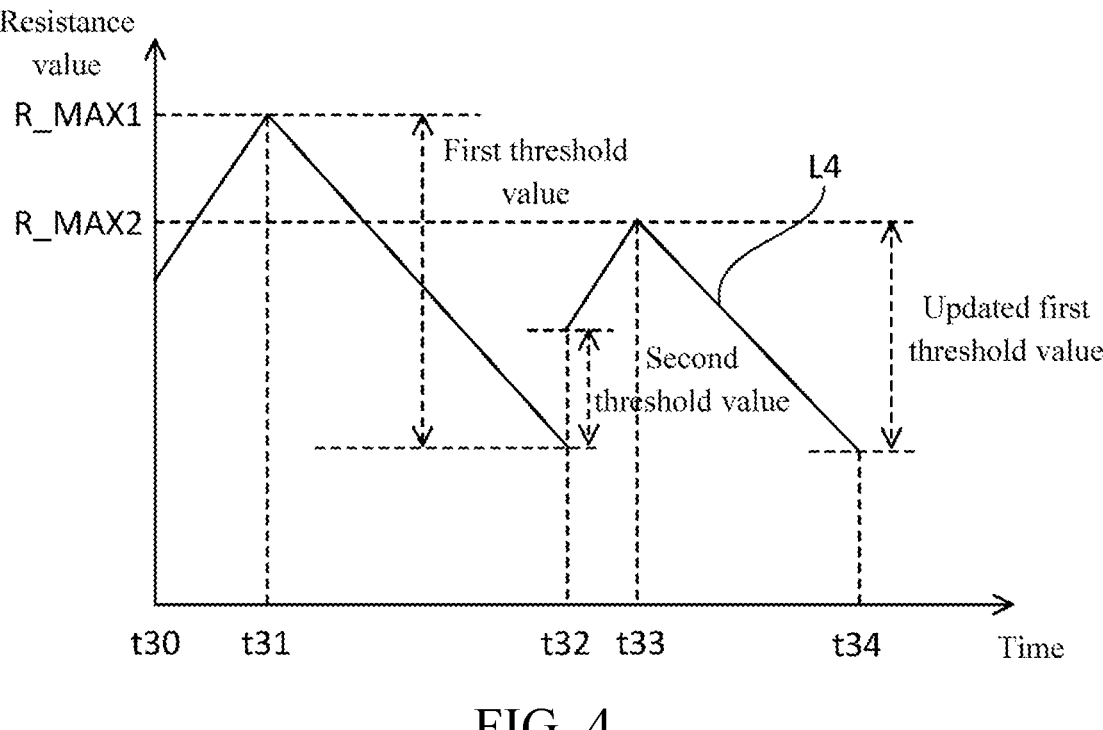
FIG. 4 is a diagram illustrating a determination criterion for the oil condition in the oil condition determination system.

FIG. 4 is a diagram illustrating a determination criterion for the oil condition in the oil condition determination system 100. Referring to FIG. 4, the horizontal axis indicates the time of use of the oil O1, and the vertical axis indicates the resistance value of the oil O1. A line L4 shows a relationship between the resistance value and the time of use of the oil O1.

During time t30 to t31, the resistance value of the oil O1 increases. At time t31, the resistance value reaches a local maximum value R_MAX1. Subsequently, the trend of change in the resistance value turns from an increase to a decrease, and during time t31 to t32, the resistance value decreases. If the difference between the local maximum value R_MAX1 and the resistance value becomes greater than or equal to the first threshold value, it is determined that the condition of the oil O1 has changed. In the oil condition determination system 100, the first threshold value is adjusted in advance according to, for example, the type and the amount of oil O1 and what is used as the oil management criterion value. If the first threshold value is properly adjusted, a notification to prompt oil replacement is issued at an appropriate timing.

In this example, at time t32, the difference between the local maximum value R_MAX1 and the resistance value becomes greater than or equal to the first threshold value. Time t32 is before the resistance value turns to an increase again. At time t32, the resistance value abruptly increases. The reason for the abrupt increase in the resistance value at time t32 will be described below.

Figure 5:
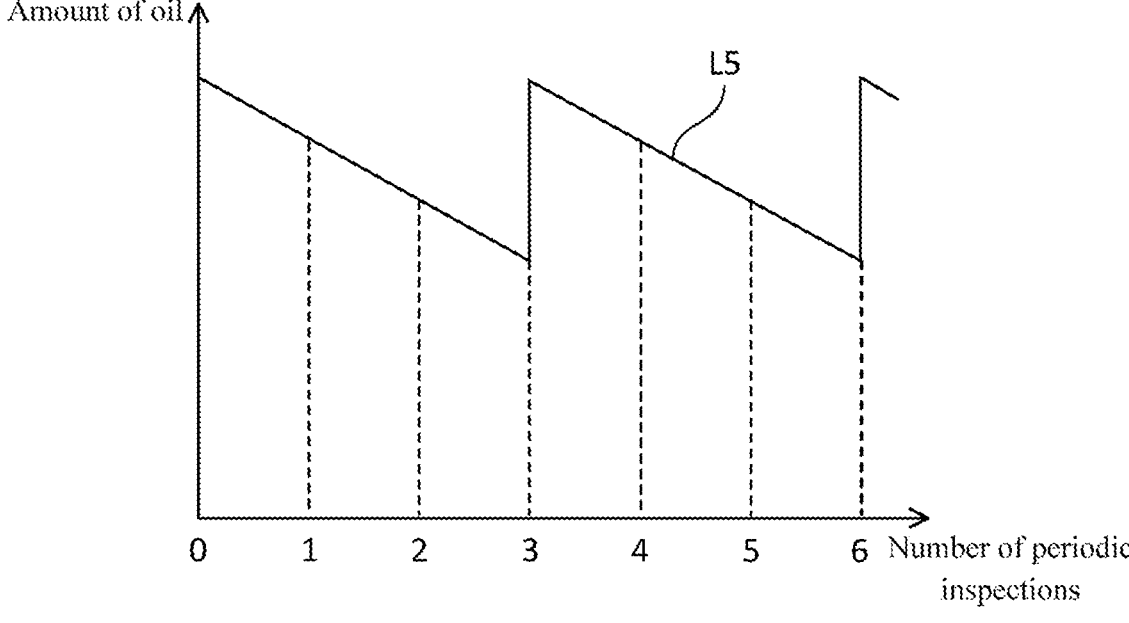
FIG. 5 is a diagram showing an example of change in the amount of oil in an oil tank.

FIG. 5 is a diagram showing an example of change in the amount of oil in the oil tank 20. Referring to FIG. 5, the horizontal axis indicates the number of periodic inspections, and the vertical axis indicates the amount of oil. Periodic inspections are performed once every 10000 hours, for example. As time elapses, the amount of oil O1 contained in the oil tank 20 decreases. In this example, the oil O1 is not added at the first, second, fourth, and fifth periodic inspections, and the oil O1 is added at the third and sixth periodic inspections.

Referring again to FIG. 4, at time t32, the oil O1 is at least either added or partially replaced. The oil O1 being partially replaced refers to part of the oil O1 contained in the oil tank 20 being replaced with new oil O1. When the oil O1 is at least either added or partially replaced, the properties of the oil O1 in the oil tank 20 change, and the resistance value of the oil O1 abruptly changes. If the oil O1 is at least either added or partially replaced, the deteriorated condition of the oil O1 is improved.

During time t32 to t33, the resistance value of the oil O1 increases. At time t33, the resistance value of the oil O1 reaches a local maximum value R_MAX2. At time t32, the entirety of the oil is not replaced, and thus the local maximum value R_MAX2 is smaller than the local maximum value R_MAX1. Subsequently, the trend of change in the resistance value reverses from an increase to a decrease, and during time t33 to t34, the resistance value decreases. That is to say, the transition of the resistance value changes due to the oil O1 being at least either added or partially replaced at time t32.

Assume that it is determined that the condition of the oil O1 has changed if the first threshold value is not updated and the difference between the local maximum value R_MAX2 and the resistance value becomes greater than or equal to the first threshold value. In this case, although a notification to prompt oil replacement has to be issued at time t34, a notification to prompt oil replacement is issued after time t34. In this manner, if the first threshold value is not updated when the oil O1 is at least either added or partially replaced, a notification to prompt oil replacement may not be issued at an appropriate timing.

In the oil condition determination system 100 according to the present embodiment, if the amount of change in the resistance value of the oil O1 per unit time becomes greater than or equal to a second threshold value, the local maximum value of the resistance value is initialized and the first threshold value is updated. The second threshold value can be said to be a threshold value for detecting that the oil O1 has been partially replaced or the oil O1 has been added. It is often the case that the oil O1 is regularly replaced and added. If the second threshold value is adjusted according to a predetermined amount regarding the amount of oil O1 replaced and added (e.g., a typical amount of oil replaced or added in regular replacement or addition), the local maximum value is initialized and the first threshold value is updated at an appropriate timing.

That is to say, when the resistance value of the oil O1 in the oil tank 20 abruptly changes due to the oil O1 being partially replaced or the oil O1 being added, the determination criterion for the oil condition is properly adjusted. Therefore, according to the oil condition determination system 100, the oil condition can be continuously and properly determined even when the oil O1 is partially replaced or the oil O1 is added.

3. Procedure for Determining Oil Condition

Figure 6:
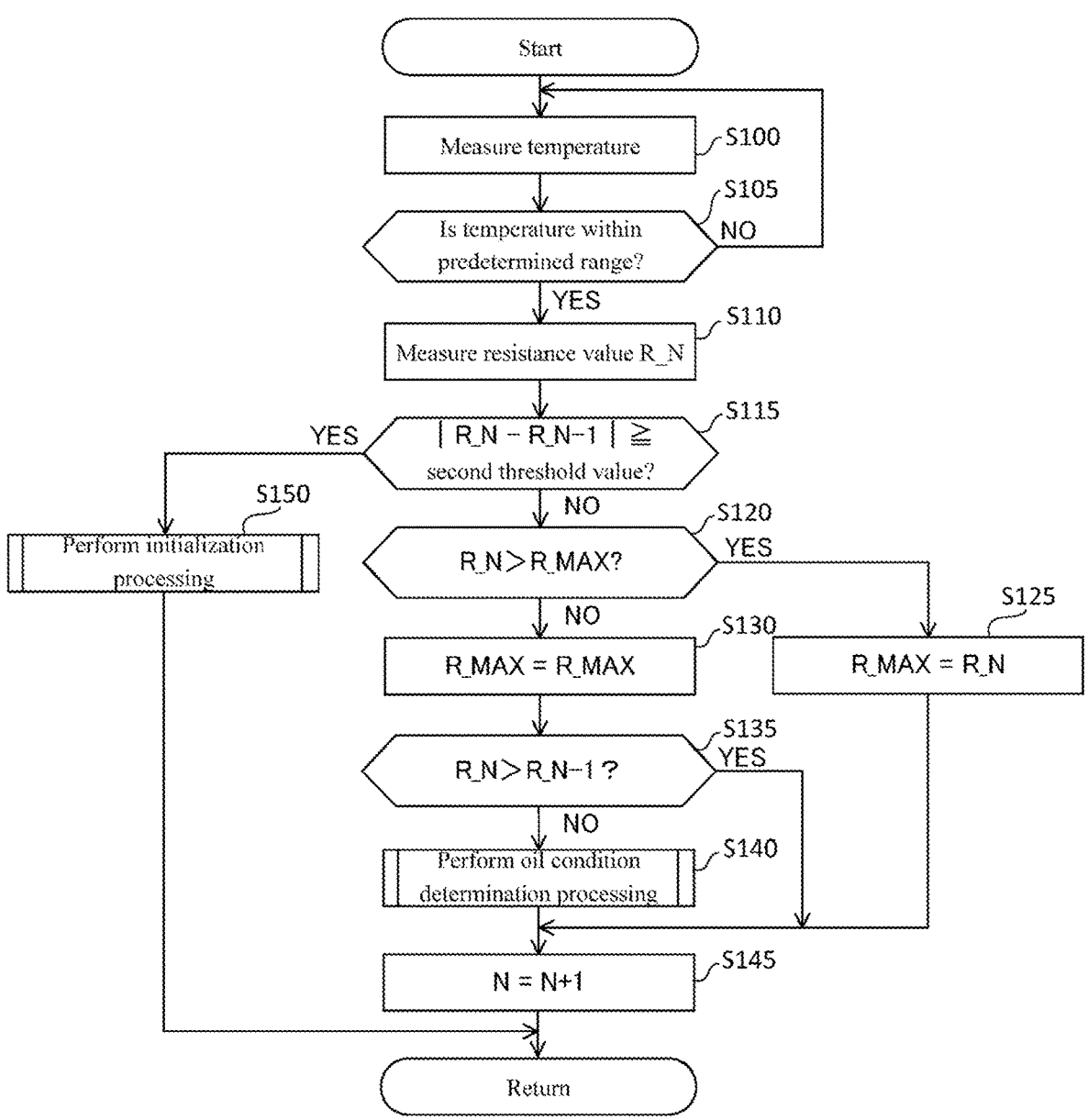
FIG. 6 is a flowchart showing a procedure for determining the oil condition in the oil condition determination system.

FIG. 6 is a flowchart showing a procedure for determining the oil condition in the oil condition determination system 100. The processing shown in this flowchart is repeatedly performed by the oil condition determination system 100 with the oil sensor 10 activated.

Referring to FIG. 6, the temperature measurement unit 108 of the oil condition determination system 100 detects a value for measuring the temperature of the oil O1 (e.g., the resistance value of the temperature sensing element 113), and the determination unit 104 of the oil condition determination system 100 measures the temperature of the oil O1 based on a detection result produced by the temperature measurement unit 108 (step S100). The determination unit 104 determines whether or not the measured temperature is within a predetermined range (step S105). The temperature of the oil O1 is taken into account because the resistance value of the oil O1 is sensitive to temperature. The predetermined range of temperature is adjusted as appropriate according to the type of oil O1, but is 30° C. to 50° C., for example.

If it is determined that the temperature of the oil O1 is not within the predetermined range ("NO" in step S105), the determination unit 104 again performs the processing in step S100. On the other hand, if it is determined that the temperature of the oil O1 is within the predetermined range ("YES" in step S105), the measurement unit 102 of the oil condition determination system 100 measures the resistance value R_N of the oil O1 (step S110). The determination unit 104 of the oil condition determination system 100 determines whether or not the absolute value of the difference between the resistance value R_N measured in the current cycle and the resistance value R_N–1 measured in the previous cycle is greater than or equal to the second threshold value (step S115).

The reason why the "absolute value" of the difference is compared with the second threshold value will be described below. When the oil O1 is partially replaced or the oil O1 is added, the resistance value of the oil O1 does not necessarily increase abruptly. Depending on the type of oil O1 or the like, the resistance value of the oil O1 may abruptly decrease when the oil O1 is partially replaced or the oil O1 is added. In order to properly detect that the oil O1 has been partially replaced or the oil O1 has been added even when the resistance value abruptly decreases, the "absolute value" of the difference is compared with the second threshold value in step S115.

If it is determined in step S115 that the absolute value of the difference between the resistance value R_N measured in the current cycle and the resistance value R_N−1 measured in the previous cycle is less than the second threshold value ("NO" in step S115), the determination unit 104 determines whether or not the resistance value R_N measured in the current cycle is greater than the currently stored local maximum value R_MAX (step S120). The local maximum value R_MAX of the resistance value is stored, for example, in the determination unit 104. If it is determined that the resistance value R_N measured in the current cycle is greater than the currently stored local maximum value R_MAX ("YES" in step S120), the determination unit 104 stores the resistance value R_N measured in the current cycle as the local maximum value R_MAX (step S125). Subsequently, the determination unit 104 performs the processing of N=N+1 (step S145), and again performs the processing in step S110.

On the other hand, if it is determined in step S120 that the resistance value R_N measured in the current cycle is less than or equal to the currently stored local maximum value R_MAX ("NO" in step S120), the determination unit 104 maintains the currently stored local maximum value R_MAX (step S130).

The determination unit 104 determines whether or not the resistance value R_N measured in the current cycle is greater than the resistance value R_N−1 measured in the previous cycle (step S135). If it is determined that the resistance value R_N measured in the current cycle is greater than the resistance value R_N−1 measured in the previous cycle ("YES" in step S135), the determination unit 104 performs the processing of N=N+1 (step S145), and again performs the processing in step S100.

On the other hand, if it is determined in step S135 that the resistance value R_N measured in the current cycle is less than or equal to the resistance value R_N−1 measured in the previous cycle ("NO" in step S135), the determination unit 104 performs oil condition determination processing (step S140). The oil condition determination processing will be described later in detail. Subsequently, the determination unit 104 performs the processing of N=N+1 (step S145), and again performs the processing in step S100.

If it is determined in step S115 that the absolute value of the difference between the resistance value R_N measured in the current cycle and the resistance value R_N−1 measured in the previous cycle is greater than or equal to the second threshold value ("YES" in step S115), the determination unit 104 performs initialization processing (step S150). The initialization processing will be described later in detail.

Figure 7:
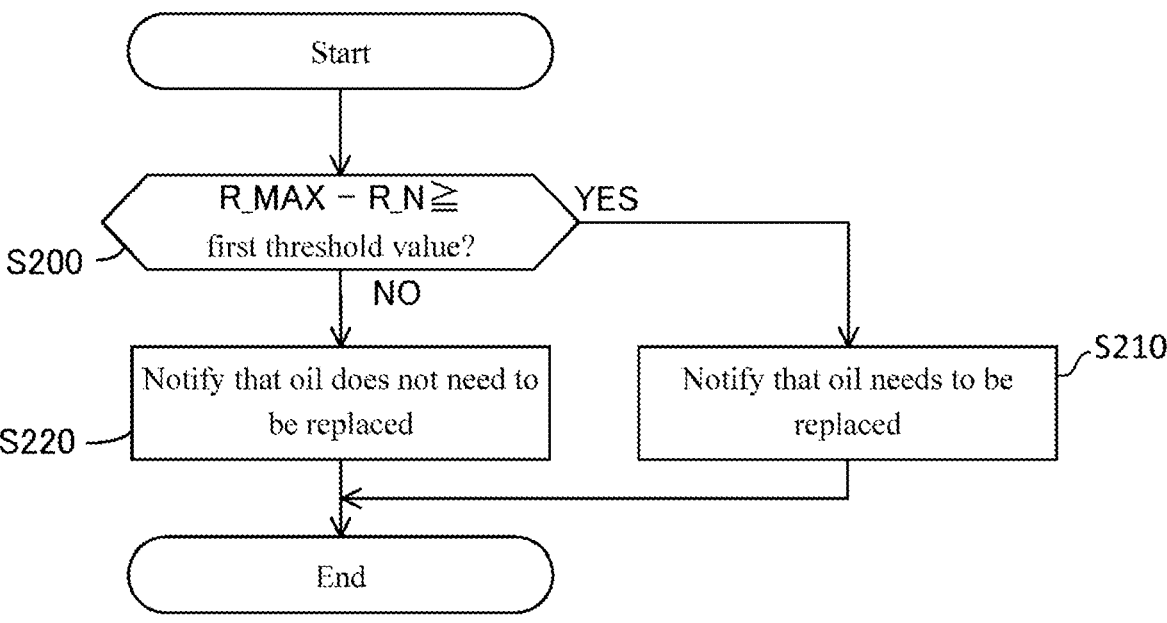
FIG. 7 is a flowchart showing a procedure of oil condition determination processing that is performed in step S140 of FIG. 6.

FIG. 7 is a flowchart showing a procedure of oil condition determination processing that is performed in step S140 of FIG. 6. The processing shown in this flowchart is performed by the oil condition determination system 100.

Referring to FIG. 7, the determination unit 104 of the oil condition determination system 100 determines whether or not the difference between the stored local maximum value R_MAX and the resistance value R_N measured in the current cycle is greater than or equal to the first threshold value (step S200). If it is determined that the difference between the stored local maximum value R_MAX and the resistance value R_N measured in the current cycle is greater than or equal to the first threshold value ("YES" in step S200), the determination unit 104 determines that the condition of the oil O1 has changed, and controls the notification unit 106 to make a notification to the effect that the oil O1 needs to be replaced (step S210).

On the other hand, if it is determined that the difference between the stored local maximum value R_MAX and the resistance value R_N measured in the current cycle is less than the first threshold value ("NO" in step S200), the determination unit 104 determines that the condition of the oil O1 has not changed, and controls the notification unit 106 to make a notification to the effect that the oil O1 does not need to be replaced (step S220). Note that if the determination result in step S200 is "NO", a notification to the effect that the oil O1 does not need to be replaced does not necessarily have to be made.

Figure 8:
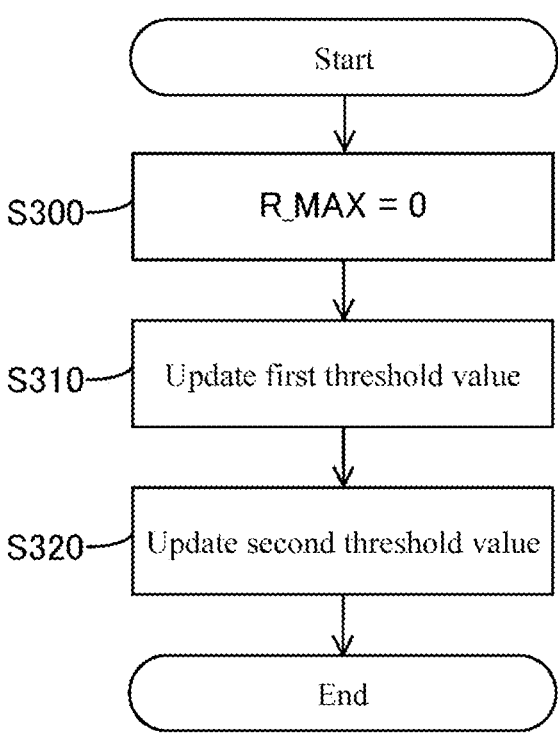
FIG. 8 is a flowchart showing a procedure of initialization processing that is performed in step S150 of FIG. 6.

FIG. 8 is a flowchart showing a procedure of initialization processing that is performed in step S150 of FIG. 6. The processing shown in this flowchart is performed by the oil condition determination system 100.

Referring to FIG. 8, the determination unit 104 of the oil condition determination system 100 initializes the local maximum value R_MAX (step S300). That is to say, the determination unit 104 performs the processing of local maximum value R_MAX=0.

The determination unit 104 updates the first threshold value according to the difference between the resistance value R_N measured in the current cycle and the resistance value R_N−1 measured in the previous cycle (step S310). The determination unit 104 estimates the amount of oil O1 replaced based on, for example, the difference between the resistance value R_N measured in the current cycle and the resistance value R_N−1 measured in the previous cycle, and updates the first threshold value based on an estimation result. For example, the larger the difference between the resistance value R_N measured in the current cycle and the resistance value R_N−1 measured in the previous cycle is, the larger the value to which the first threshold value is updated is.

The determination unit 104 updates the second threshold value according to the difference between the resistance value R_N measured in the current cycle and the resistance value R_N−1 measured in the previous cycle (step S320). For example, the larger the difference between the resistance value R_N measured in the current cycle and the resistance value R_N−1 measured in the previous cycle is, the larger the value to which the determination unit 104 updates the second threshold value is.

In this manner, in the oil condition determination system 100, if the amount of change in the resistance value of the oil O1 per unit time becomes greater than or equal to the second threshold value, the local maximum value is initialized and the first threshold value is updated. That is to say, when the resistance value abruptly changes due to the oil O1 being partially replaced or the oil O1 being added, the determination criterion for the oil condition is properly changed. Therefore, according to the oil condition determination system 100, the oil condition can be continuously and properly determined even when the oil O1 is partially replaced or the oil O1 is added.

Furthermore, when the oil O1 is partially replaced or the oil O1 is added, the transition of the resistance value of the oil O1 changes in accordance with the amount of oil O1 replaced or the amount of oil O1 added. According to the oil condition determination system 100, the first threshold value is updated based on the amount of change in the resistance value due to the oil O1 being replaced or added, and the determination criterion for the oil condition is more properly changed. Accordingly, the oil condition can be more properly determined.

Furthermore, according to the oil condition determination system 100, if it is determined that the condition of the oil O1 has changed, the user is notified that the oil O1 needs to be replaced, and thus the user can be prompted to replace oil at the time at which oil replacement becomes necessary.

4. Features

As described above, in the oil condition determination system 100 according to the present embodiment, if the amount of change in the resistance value of the oil O1 per unit time becomes greater than or equal to the second threshold value, the local maximum value is initialized and the first threshold value is updated. That is to say, when the resistance value abruptly changes due to the oil O1 being partially replaced or the oil O1 being added, the determination criterion for the oil condition is properly changed. Therefore, according to the oil condition determination system 100, the oil condition can be continuously and properly determined even when the oil O1 is partially replaced or the oil O1 is added.

5. Other Embodiments

The idea of the embodiments is not limited to the embodiments described above. As one example, at least part of the configuration of any of the embodiments may be combined with at least part of the configuration of any of the other embodiments. Examples of other embodiments to which the idea of the foregoing embodiments can be applied are described below.

<5-1>

Figure 9:
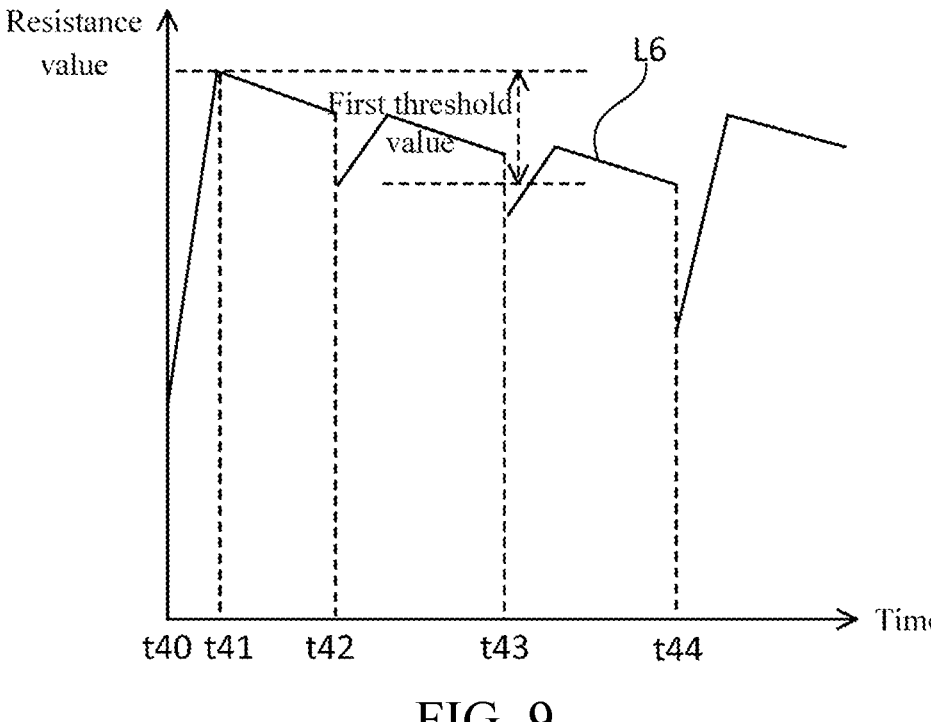
FIG. 9 is a diagram illustrating a determination criterion for a change in the condition of oil in a first alternative embodiment.

FIG. 9 is a diagram illustrating a determination criterion for a change in the condition of oil in a first alternative embodiment. Referring to FIG. 9, the horizontal axis indicates the time of use of the oil O1, and the vertical axis indicates the resistance value of the oil O1. A line L6 shows a relationship between the resistance value and the time of use of the oil O1.

During time t40 to t41, the resistance value of the oil O1 increases. At time t41, the resistance value reaches a local maximum value. Subsequently, the trend of change in the resistance value turns from an increase to a decrease, and during time t41 to t42, the resistance value decreases. At time t42, for example, the oil O1 is added, and the resistance value abruptly decreases. However, at time t42, the amount of decrease in the resistance value is less than the second threshold value. Therefore, for example, the local maximum value is not initialized. During time t42 to t43, the resistance value increases and then turns to a decrease.

At time t43, for example, the oil O1 is again added, and the resistance value abruptly decreases. At time t43, the difference between the local maximum value and the resistance value becomes greater than or equal to the first threshold value. However, at time t43 and thereafter, the resistance value increases. Therefore, at time t43, the oil O1 does not have to be replaced immediately. In the first alternative embodiment, even when a difference between the local maximum value and the resistance value becomes greater than or equal to the first threshold value, a notification to the effect that the oil O1 needs to be replaced is not made if the resistance value increases thereafter.

Figure 10:
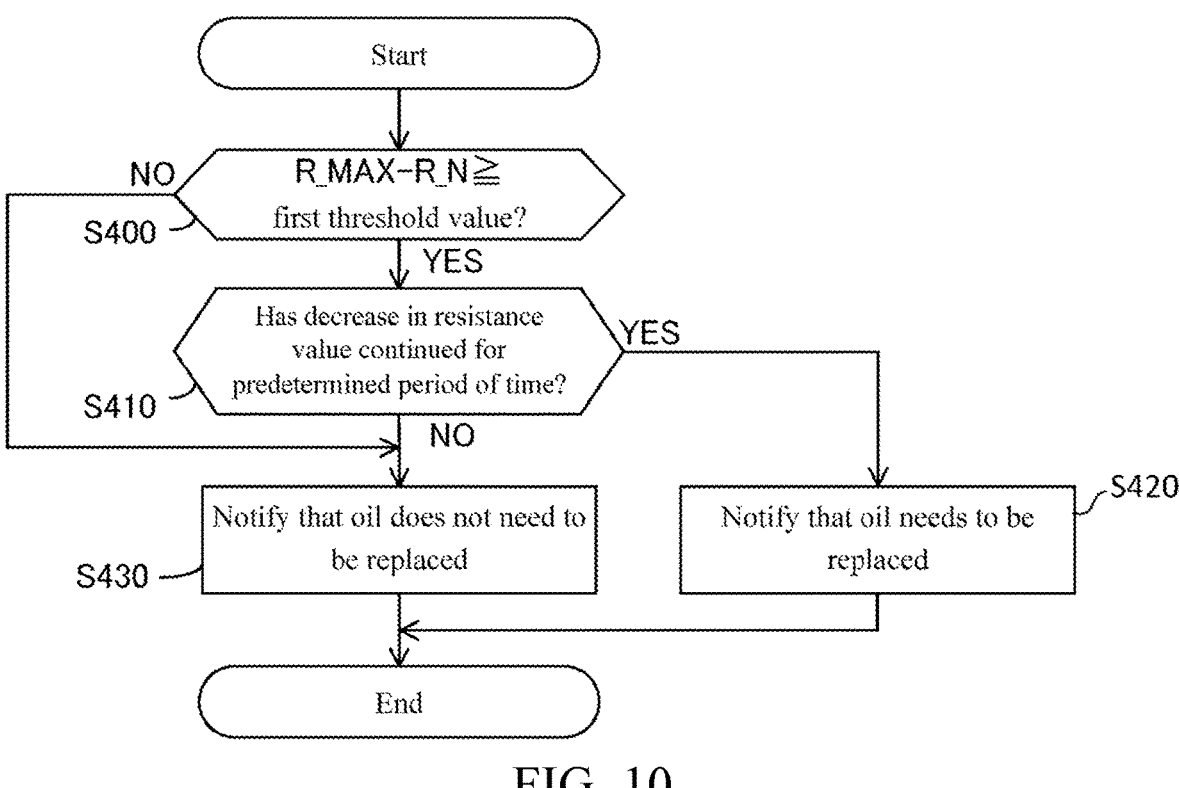
FIG. 10 is a is a flowchart showing a procedure of oil condition determination processing that is performed in step S140 of FIG. 6 in the first alternative embodiment.

FIG. 10 is a flowchart showing a procedure of oil condition determination processing that is performed in step S140 of FIG. 6 in the first alternative embodiment. The processing shown in this flowchart is performed by the oil condition determination system 100. Note that in the first alternative embodiment, the processing in step S110 included in the flowchart in FIG. 6 is omitted, and the resistance value of the oil O1 is measured in parallel with the processing in the flowchart in FIG. 6. The cycle for measuring the resistance value is shorter than the cycle in which the processing shown in the flowchart in FIG. 10 is performed.

Referring to FIG. 10, the determination unit 104 of the oil condition determination system 100 determines whether or not the difference between the stored local maximum value R_MAX and the resistance value R_N measured in the current cycle is greater than or equal to the first threshold value (step S400). If it is determined that the difference between the stored local maximum value R_MAX and the resistance value R_N measured in the current cycle is greater than or equal to the first threshold value ("YES" in step S400), the determination unit 104 determines whether or not the trend of decrease in the resistance value has continued for a predetermined period of time (step S410).

If it is determined that the trend of decrease in the resistance value has continued for the predetermined period of time ("YES" in step S410), the determination unit 104 controls the notification unit 106 to make a notification to the effect that the oil O1 needs to be replaced (step S420). On the other hand, if it is determined that the trend of decrease in the resistance value has not continued for the predetermined period of time ("NO" in step S410), the determination unit 104 controls the notification unit 106 to make a notification to the effect that the oil O1 does not need to be replaced (step S430). Note that the predetermined period of time is, for example, the period during which the resistance value is measured three or more times.

As described above, the resistance value of the oil O1 may temporarily decrease and then turn to an increase due to the oil O1 being added. Even when a difference between the local maximum value and the resistance value becomes greater than or equal to the first threshold value due to the resistance value of the oil O1 temporarily decreasing, it is not always appropriate to determine that the condition of the oil O1 has changed if the resistance value increases thereafter. According to the oil condition determination system 100 in the first alternative embodiment, even when a difference between the local maximum value and the resistance value becomes greater than or equal to the first threshold value, it is not determined that the condition of the oil O1 has changed if a decrease in the resistance value has not continued for the predetermined period of time, and thus the occurrence of the above-mentioned inappropriate situation can be suppressed.

<5-2>

In the foregoing embodiment, if a difference between the local maximum value and the resistance value becomes greater than or equal to the first threshold value, it is determined that the condition of the oil O1 has changed. However, the determination criterion for a change in the condition of the oil O1 is not limited thereto. For example, it may be determined that the condition of the oil O1 has changed if a difference between the local maximum value and the resistance value becomes greater than or equal to the first threshold value and the trend of change in the resistance value turns from a decrease to an increase.

Figure 11:
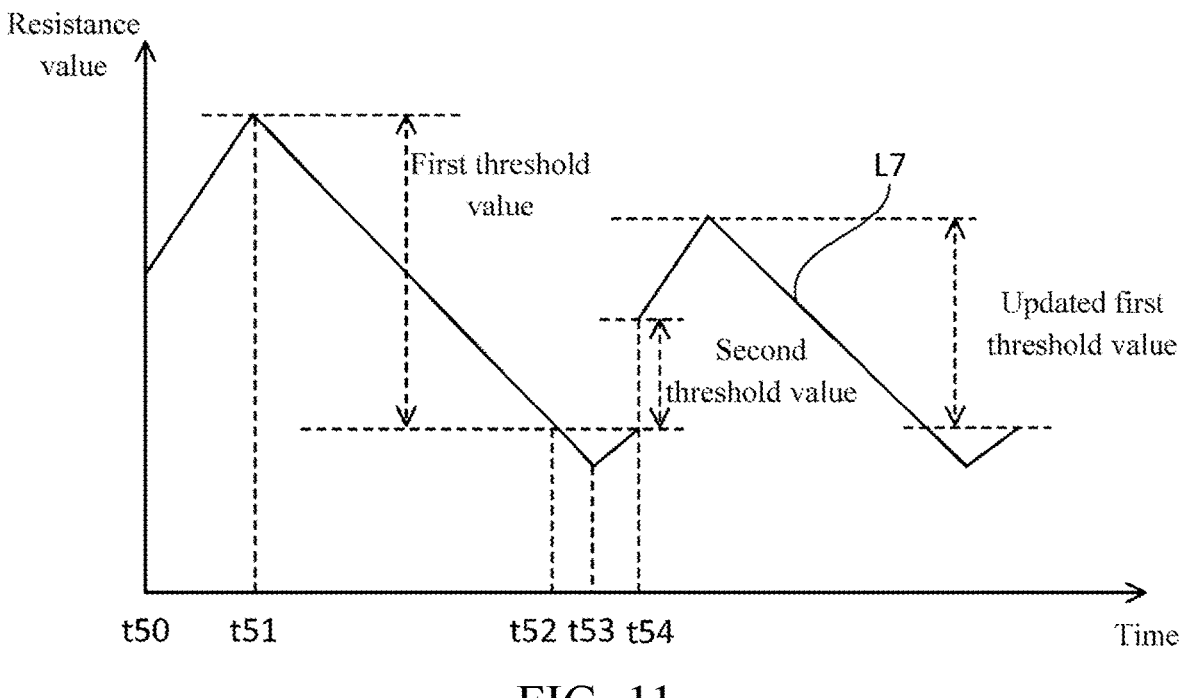
FIG. 11 is a diagram illustrating a determination criterion for a change in the condition of oil in a second alternative embodiment.

FIG. 11 is a diagram illustrating a determination criterion for a change in the condition of the oil O1 in a second alternative embodiment. Referring to FIG. 11, the horizontal axis indicates the time of use of the oil O1, and the vertical axis indicates the resistance value of the oil O1. A line L7 shows a relationship between the resistance value and the time of use of the oil O1.

At time t51, the resistance value reaches a local maximum value, and, at time t52, the difference between the resistance value and the local maximum value becomes greater than or equal to the first threshold value. In the second alternative embodiment, it is not determined at time t52 that the condition of the oil O1 has changed.

At time t53, the trend of change in the resistance value turns from a decrease to an increase, and, at time t54, it is detected that the trend of change in the resistance value turns from a decrease to an increase. For example, at time t54, it may be determined that the condition of the oil O1 has changed.

<5-3>

In the foregoing embodiment, only the first threshold value is provided as the threshold value for a difference between the local maximum value of the resistance value and the current resistance value. However, the threshold value may be provided in a stepwise manner. If the threshold value may be provided in a stepwise manner, the degree of deterioration of the oil O1 can be detected in a stepwise manner.

<5-4>

In the foregoing embodiment, the determination unit 104 may store time information indicating when the resistance value reached a local maximum value and time information indicating when the resistance value reached a local mini- mum value. The determination unit 104 may calculate the slope of the change in the resistance value based on these pieces of time information, the local maximum value, and the local minimum value, and analyze deterioration of the oil O1 based on the slope of the change in the resistance value. The determination unit 104 may calculate the slope of the change in the resistance value after the trend of change in the resistance value turns from an increase to a decrease, and predict the time at which the oil O1 needs to be replaced based on the slope of the change in the resistance value. The notification unit 106 may make a notification regarding the predicted time at which the oil O1 needs to be replaced.

<5-5>

In the foregoing embodiment, the type of oil O1 may be estimated based on the amount of change in the resistance value per unit time after the oil O1 is replaced and the local maximum value of the resistance value after the oil O1 is replaced.

<5-6>

In the foregoing embodiment, if the resistance value of the oil O1 abruptly changes and the resistance value does not change at least for a predetermined period of time thereafter, the determination unit 104 may determine that an error has occurred and that the condition of the oil O1 has changed. For example, when a large amount of moisture is mixed in the oil tank 20, when a short circuit caused by a conductive material occurs between the pair of electrodes 112, or when the oil sensor 10 malfunctions, a situation may occur in which the resistance value of the oil O1 abruptly changes and the resistance value does not change at least for a predetermined period of time thereafter.

<5-7>

In the foregoing embodiment, if a change in the tempera- ture of the oil O1 is detected and a change in the resistance value of the oil O1 is not detected, the determination unit 104 may determine that an error has occurred and that the condition of the oil O1 has changed. For example, when a short circuit caused by a conductive material occurs between the pair of electrodes 112 or when the oil sensor 10 mal- functions, a situation may occur in which a change in the resistance value of the oil O1 is not detected even when the temperature has changed.

<5-8>

In the foregoing embodiment, the determination unit 104 and the notification unit 106 are included in the oil sensor 10. However, the determination unit 104 and the notification unit 106 do not necessarily have to be included in the oil sensor 10. At least one of the determination unit 104 and the notification unit 106 may be provided in an apparatus that uses the oil sensor 10.

<5-9>

In the foregoing embodiment, when the power supply to the oil sensor 10 is stopped, a difference between the local maximum value of the resistance value and the current resistance value before the power supply was stopped may be calculated after the power supply to the oil sensor 10 is resumed, and if the difference is greater than or equal to the first threshold value, the initialization processing shown in step S150 of FIG. 6 may be performed. Note that the local maximum value of the resistance value of the oil O1 before the power supply is stopped is stored, for example, in a non-volatile memory included in the determination unit 104.

<5-10>

In the foregoing embodiment, the oil sensor 10 may further include a battery (cell). The oil sensor 10 may be configured to be driven by power supplied from the battery, for example, during a power failure.

Figure 12:
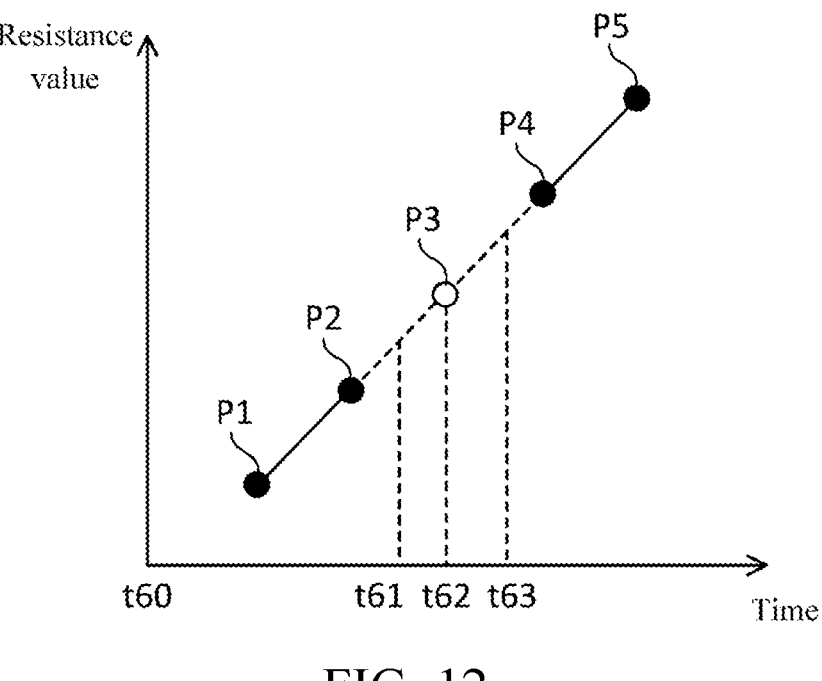
FIG. 12 is a diagram illustrating a first example of the advantages of driving with a battery during a power failure.

FIG. 12 is a diagram illustrating a first example of the advantages of driving with a battery during a power failure. Referring to FIG. 12, the horizontal axis indicates the time of use of the oil O1, and the vertical axis indicates the resistance value of the oil O1. Each of the points P1, P2, P4, and P5 corresponds to the resistance value measured with the oil sensor 10 being driven by the power from the system power supply. On the other hand, the point P3 corresponds to the resistance value measured during a power failure. For example, a power failure occurs at time t61, the resistance value is measured at time t62, and the power supply from the system power supply is resumed at time t63. In this manner, the driving with a battery during a power failure makes it possible to measure the resistance value of the oil O1 even during a power failure.

Figure 13:
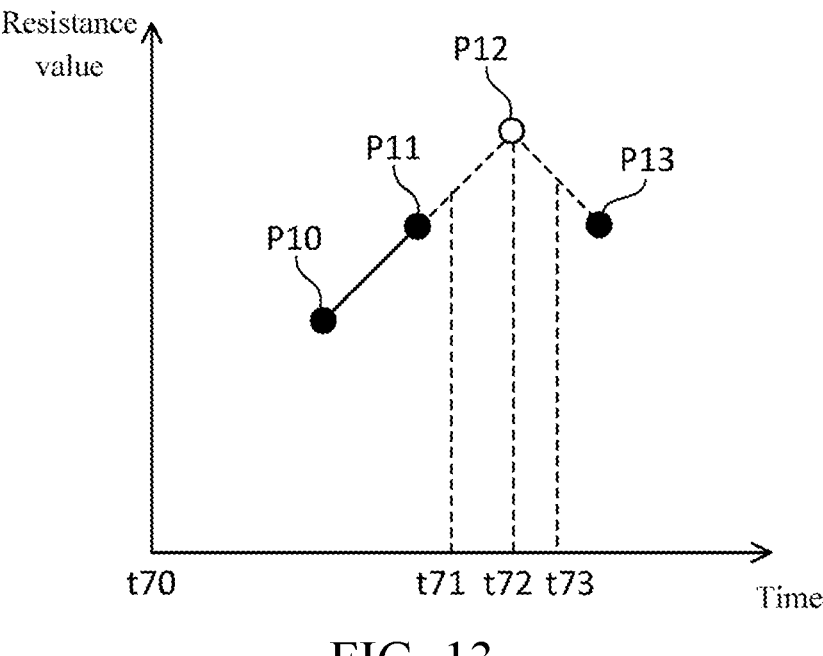
FIG. 13 is a diagram illustrating a second example of the advantages of driving with a battery during a power failure.

FIG. 13 is a diagram illustrating a second example of the advantages of driving with a battery during a power failure. Referring to FIG. 13, the horizontal axis indicates the time of use of the oil O1, and the vertical axis indicates the resistance value of the oil O1. Each of the points P10, P11, and P13 corresponds to the resistance value measured with the oil sensor 10 being driven by the power from the system power supply. On the other hand, the point P12 corresponds to the resistance value measured during a power failure. For example, a power failure occurs at time t71, the resistance value of the oil O1 is resumed at time t72, and the power supply from the system power supply is resumed at time t73. The resistance value at time t72 is a local maximum value. In this manner, the driving with a battery during a power failure makes it possible to avoid the occurrence of a situation in which the local maximum value of the resistance value cannot be measured during a power failure.

Several embodiments of the present invention have been described above as examples. That is, the detailed descrip- tion and attached drawings are provided for illustrative purposes. Accordingly, the constituent elements indicated in the detailed description and the attached drawings may include constituent elements that are not essential for solv- ing the technical problem. Accordingly, the inclusion of such non-essential constituent elements in the detailed descrip- tion and attached drawings should not be interpreted as non-essential constituent elements being essential.

The embodiments described above are exemplary in all aspects of the present invention. The embodiments described above can be subjected to various changes and modifications within the scope of the present invention. That is, when implementing the present invention, it is possible to use an appropriate specific configuration in keeping with that particular implementation.

LIST OF REFERENCE NUMERALS

10 Oil sensor
20 Oil tank
100 Oil condition determination system
102 Measurement unit
104 Determination unit
106 Notification unit
108 Temperature measurement unit
110 Substrate
111 Substrate body
112 Electrode
113 Temperature sensing element
L1-L7 Line
O1 Oil
P1-P5, P10-P13 Point

The invention claimed is:

1. An oil condition determination system comprising:
a measurement unit configured to periodically measure a resistance value of oil; and
a determination unit configured to periodically determine a condition of the oil based on the resistance value,
wherein the determination unit
stores a local maximum value of the resistance value,
determines that the condition of the oil has changed in a case in which a difference between the local maximum value and the resistance value becomes greater than or equal to a first threshold value, and
initializes the local maximum value and updates the first threshold value in a case in which the amount of change in the resistance value per unit time becomes greater than or equal to a second threshold value.

2. The oil condition determination system according to claim 1, wherein the determination unit updates the first threshold value based on the amount of change in a case in which the amount of change becomes greater than or equal to the second threshold value.

3. The oil condition determination system according to claim 1, further comprising a notification unit configured to notify a user that the oil needs to be replaced in a case in which the determination unit determines that the condition of the oil has changed.

4. The oil condition determination system according to claim 1, wherein, in a case in which a difference between the local maximum value and the resistance value becomes greater than or equal to the first threshold value,
the determination unit
determines that the condition of the oil has changed when a decrease in the resistance value has continued for a predetermined period of time, and does not determine that the condition of the oil has changed when a decrease in the resistance value has not continued for the predetermined period of time.

5. The oil condition determination system according to claim 1, wherein the determination unit determines that the condition of the oil has changed in a case in which a difference between the local maximum value and the resistance value becomes greater than or equal to the first threshold value and a trend of change in the resistance value reverses.

6. An oil condition determination method comprising:
a step of periodically measuring a resistance value of oil; and
a step of periodically determining a condition of the oil based on the resistance value,
wherein the step of periodically determining a condition of the oil includes:
a step of storing a local maximum value of the resistance value;
a step of determining that the condition of the oil has changed in a case in which a difference between the local maximum value and the resistance value becomes greater than or equal to a first threshold value; and
a step of initializing the local maximum value and updating the first threshold value in a case in which the amount of change in the resistance value per unit time becomes greater than or equal to a second threshold value.

7. The oil condition determination system according to claim 2, further comprising a notification unit configured to notify a user that the oil needs to be replaced in a case in which the determination unit determines that the condition of the oil has changed.

8. The oil condition determination system according to claim 2, wherein, in a case in which a difference between the local maximum value and the resistance value becomes greater than or equal to the first threshold value,
the determination unit
determines that the condition of the oil has changed when a decrease in the resistance value has continued for a predetermined period of time, and
does not determine that the condition of the oil has changed when a decrease in the resistance value has not continued for the predetermined period of time.

9. The oil condition determination system according to claim 2, wherein the determination unit determines that the condition of the oil has changed in a case in which a difference between the local maximum value and the resistance value becomes greater than or equal to the first threshold value and a trend of change in the resistance value reverses.

* * * * *